(12) United States Patent
Brown et al.

(10) Patent No.: US 8,503,608 B2
(45) Date of Patent: Aug. 6, 2013

(54) RADIOTHERAPEUTIC APPARATUS

(75) Inventors: Kevin Brown, West Sussex (GB); Ralph Streamer, West Sussex (GB); Paul Boxall, Crawley (GB); Duncan Bourne, Surrey (GB); Christopher James Gibson, Surrey (GB)

(73) Assignee: Elekta AB (Publ), Stockholm (SE)

( * ) Notice: Subject to any disclaimer, the term of this patent is extended or adjusted under 35 U.S.C. 154(b) by 369 days.

(21) Appl. No.: 12/739,206

(22) PCT Filed: Oct. 24, 2007

(86) PCT No.: PCT/EP2007/009227
§ 371 (c)(1),
(2), (4) Date: Sep. 14, 2010

(87) PCT Pub. No.: WO2009/052845
PCT Pub. Date: Apr. 30, 2009

(65) Prior Publication Data
US 2010/0329422 A1    Dec. 30, 2010

(51) Int. Cl.
*A61N 5/10* (2006.01)
(52) U.S. Cl.
USPC .......................................................... 378/65
(58) Field of Classification Search
USPC .......................................................... 378/65
See application file for complete search history.

(56) References Cited

U.S. PATENT DOCUMENTS

| | | | |
|---|---|---|---|
| 5,818,902 A | 10/1998 | Yu | |
| 6,853,705 B2 * | 2/2005 | Chang | 378/65 |
| 6,907,105 B2 * | 6/2005 | Otto | 378/65 |
| 6,999,556 B2 * | 2/2006 | Nakano | 378/65 |
| 7,734,010 B2 * | 6/2010 | Otto et al. | 378/65 |
| 7,906,770 B2 * | 3/2011 | Otto | 250/492.3 |
| 7,961,843 B2 * | 6/2011 | Brown et al. | 378/65 |
| 2003/0086530 A1 | 5/2003 | Otto | |
| 2004/0184578 A1 | 9/2004 | Nakano | |

FOREIGN PATENT DOCUMENTS

WO    9713552    4/1997

OTHER PUBLICATIONS

Duthoy, W., et al., "Clinical Implementation of Intensity-Modulated Arc Therapy (IMAT) for Rectal Cancer" International Journal of Radiation: Oncology Biology Physics, Pergamon Press, U.S., vol. 60, No. 3, Nov. 1, 2004, pp. 794-806.
PCT International Search Report, Feb. 12, 2008.

\* cited by examiner

*Primary Examiner* — Allen C. Ho
(74) *Attorney, Agent, or Firm* — Westman, Champlin & Kelly, P.A.; Z. Peter Sawicki

(57) ABSTRACT

Apparatus comprising a radiation source which can rotate in an arc around the radiation beam axis, a multi-leaf collimator (MLC), and a controller for the source dose/time rate, the source rotation speed, and the MLC position. The controller calculates the time required for (i) an MLC leaf movement from start to end of an arc-segment at a maximum leaf speed, (ii) rotation of the source from start to end of the arc-segment at a maximum speed, and (iii) delivery of the dose at a maximum dose rate per time, selects the longest of (i), (ii) and (iii), and operates the selected one at its maximum and the others at a reduced rate matching that longest time, the time required for (i) and/or (ii) being the greater of the time to complete the segment at a continuous speed and the time to accelerate the item to that speed.

22 Claims, 5 Drawing Sheets

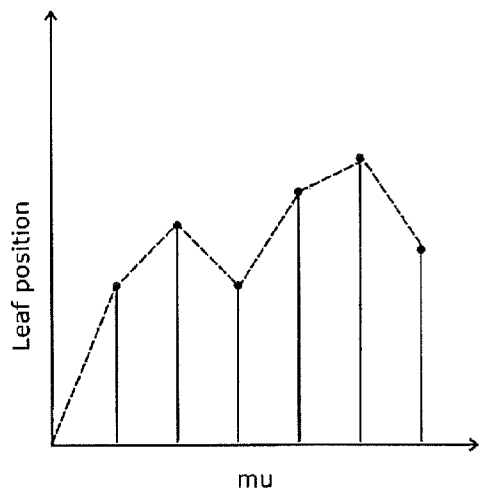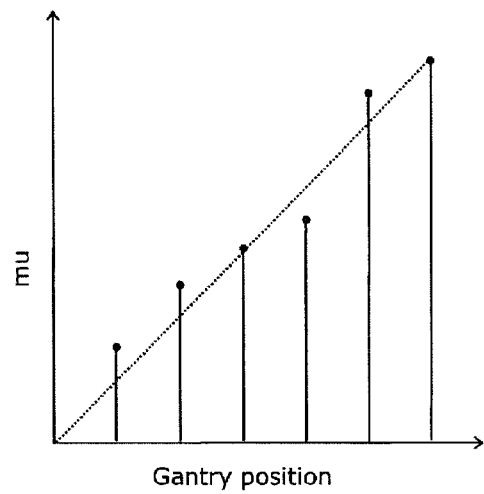
Fig 1  Fig 2
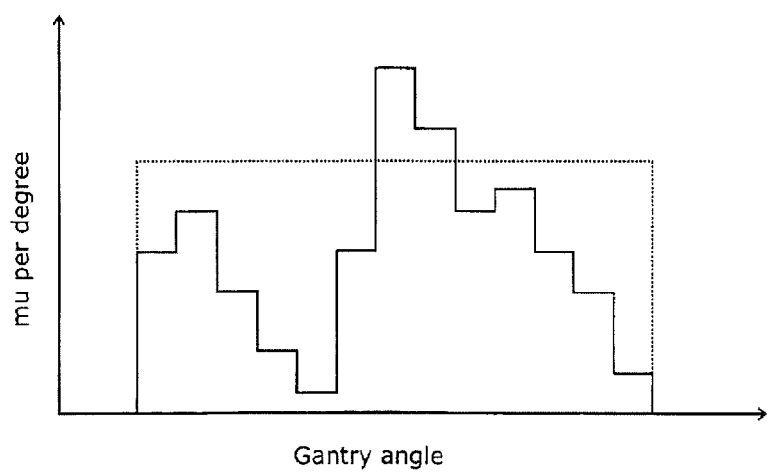
Fig 3 mu per degree mu per degree

RADIOTHERAPEUTIC APPARATUS

This Application is a Section 371 National Stage Application of International Application No. PCT/EP2007/009227, filed Oct. 24, 2007 and published as WO 2009/052845 A1 on Apr. 30, 2009, the content of which is hereby incorporated by reference in its entirety.

FIELD OF THE INVENTION

The present invention relates to radiotherapeutic apparatus.

BACKGROUND ART

A radiotherapeutic apparatus is typically controlled by a Treatment Control Computer. When equipped with a Multi-Leaf Collimator ("MLC") the Treatment Control Computer can be considered to contain a Radiation Control Computer which controls the radiation generation, an MLC Control computer which controls the shape of the MLC and a Gantry Control Computer which controls the position of the Gantry. These computers may physically be one or more computers but in this text are considered as distinct functional elements of the system. "Mu" is an abbreviation for "monitor units", which is the term used for units of radiation from the radiotherapeutic apparatus. An mu is equivalent to a unit of dose delivered to the patient under well defined calibration conditions. The relationship between mu and dose is modelled in the Treatment planning computer. The user interacts with the patient's prescription in units of dose but the Treatment planning computer defines the Treatment plan in units of mu. One of the tasks of a Treatment Planning computer is to ascertain the mu that need to be delivered by the apparatus in order to achieve a specific dose within the patient, both in terms of a sufficiently high dose in the tumour site and a sufficiently low dose in other parts of the patient. Informally, the use of the term 'dose rate' means 'mu rate'

Intensity Modulated Radiotherapy is a generic term for a number of radiotherapy techniques that, essentially, vary the beam that is directed at the patient. That variation can be spatial, temporal, or both.

Known linac delivery technologies include the following.

Segmental or Static Multi-Leaf Collimator—"SMLC"—is where the Multi-Leaf Collimator ("MLC") is static during irradiation. The MLC moves from one shape to the next in between irradiations. In one architecture, the point at which the irradiation stops and the MLC moves is controlled by the dosimetry hardware and Radiation Control computer. This results in exceptionally accurate delivery of dose per MLC shape. An alternative system uses a DMLC architecture to achieve the same effect. The MLC Control computer monitors the delivered dose and inhibits radiation when it detects it should move from one shape to the next. The inevitable control system delays associated with this architecture result in an uncertain dose per MLC shape and occasional missed shapes altogether.

Dynamic MLC—DMLC—is where the MLC moves during irradiation, with the gantry stationary. The MLC moves linearly from one shape to the next as a function of the delivered dose. The MLC control system has to monitor the delivered dose, and there is an inevitable delay. On older systems this delay was 200-300 ms, for more recent systems this is approximately 40 to 50 ms. This delay, together with the response of the MLC, results in the shapes lagging behind the dose. This is extensively reported in the literature, but is widely regarded as not being clinically significant.

Rotational DMLC—RDMLC—is where the MLC moves during irradiation during a constant rotation of the gantry. The gantry moves at a constant mu per degree. The MLC moves linearly from one shape to the next as a function of the delivered dose. The shapes are usually, but not necessarily, defined at regular intervals around the arc. This can be achieved with a substantially independent MLC, Radiation and Gantry control computers.

Enhanced Rotational DMLC—ERDMLC—is where the MLC moves during irradiation during a rotation of the gantry and the gantry moves at a variable mu per degree. A variable gantry speed or variable dose rate (or both) can achieve the latter. Using variable dose rate alone has been analysed by the University of Gent as not being the preferred option as it gives longer delivery times. The MLC moves linearly from one shape to the next as a function of the delivered dose. The shapes and doses are usually, but not necessarily, defined at regular intervals around the arc. This technique requires a very high degree of integration between the MLC, Radiation and Gantry control computers and, to date, no linac has been able to deliver ERDMLC. At present, it is therefore a theoretical possibility only.

Treatment techniques involve a compatible treatment planning function and Linac delivery function, and known techniques are as follows:

Intensity Modulated Radiation Therapy—IMRT—is a sequence of MLC shapes with associated doses which can be delivered using SMLC and DMLC. The shapes are defined at a limited number of stationary gantry positions, typically 5 to 9. The shapes and doses are defined by an optimiser which attempts to meet objectives defined by the user. The treatment planning function is generally specific to the MLC constraints and the delivery technique.

Rotational Conformal Arc Treatments—RCAT—involves a constant rotation of the Gantry while the leaves are fitted dynamically to the projection of the target volume. This technique has been in use in Japan for many years. The delivery technique is RDMLC and only one arc is used.

Intensity Modulated Arc Therapy—IMAT—involves a treatment planning function in which the arcs and the positions of the leaves are not defined by the projection of the target volume but by an optimisation routine that tries to deliver the required dose distribution to the target and critical structures. In general a number of arcs are used over different ranges of gantry angles. The optimisation is like IMRT but includes the added flexibility of the rotational gantry. IMAT can be delivered via RDMLC, but this imposes a restriction on the optimisation of a constant mu per degree, which results in a sub-optimal plan. More ideally, the optimisation will be allowed complete freedom and an ERDMLC delivery technique will be used. The delivery times are exceptionally quick, typically 3 minutes for a complex plan. Superficially this technique looks the same as RCAT but the difference is how the MLC shapes are determined.

IMAT is discussed, for example, in Duthoy et al, "Clinical implementation of intensity-modulated arc therapy (IMAT) for rectal cancer", International Journal of Radiation Oncology, Volume 60, Issue 3, 1 Nov. 2004, pp 794-806 which ends "We identified significant potential for improvements both at the levels of planning and delivery. The single most important technical improvement for IMAT is the implementation of a variable gantry speed", i.e. an apparatus capable of ERDMLC.

Optimized Segment-Aperture Mono-Arc Therapy—OSAMAT—is a special class of IMAT in which only one arc is used. This seems suitable for some clinical indications. It could also be regarded as a refinement of RCAT. Similar to IMAT the delivery technique can be simply RDMLC but more ideally ERDMLC. The delivery times are exceptionally quick, typically 1 minute.

Arc Modulation Optimisation Algorithm—AMOA—is the technique used by 3D Line Medical Systems. The leaf shapes are defined by the anatomy (as in RCAT) and then the arcs are divided into smaller sub arcs of about 20 degrees and the weight or mu per degree of these sub arcs are optimised to give the best dose distribution (similar to IMAT or IMRT). Thus, this is a form of IMAT or OSAMAT in which the option of modifying the leaf positions is not used. This is very quick to plan and to deliver, especially using the ERDMLC delivery technique.

Helical Intensity Modulated Arc Therapy—HIMAT—is a development of the IMAT technique where the patient is translated longitudinally simultaneously with the gantry rotation. This effectively makes the longitudinal length of the treatable field unlimited and truly competes with a Tomotherapy delivery solution. U.S. Pat. No. 5,818,902 and WO97/13552 show details of this. This typically has an MLC in a fixed orientation with the leaves moving across the patient. The MLC can have high-resolution leaves and a limited field size, as the field size can be extended by use of the helical technique.

The delivery technique for HIMAT can be simply RDMLC as the multiple rotations will allow the flexibility of increased dose from certain angles. The delivery times are exceptionally quick, typically 3 minutes for a complex plan.

Our earlier application PCT/EP2006/003901 proposed a methodology by which a close approximation to ERDMLC could be achieved in practice. The present application describes this methodology and explains how it can be refined to take account of the dynamic properties of the apparatus on which it is embodied.

SUMMARY OF THE INVENTION

It is possible that the ERDMLC delivery technique will give advantages, particularly to IMAT and HIMAT treatment plans. However, it has not proved possible to deliver ERDMLC in practice. A delivery technology that approximated to ERDMLC in terms of its capabilities but which was technically feasible to deliver would therefore be of great value.

Historically, all arcs have been delivered at a nominally constant rotation speed and constant dose rate, giving a fixed mu per degree of rotation. This requires constraints to be placed on the treatment planning optimisation which degrade the clinical quality of the plan. Further, there is a maximum speed at which the leaves of the multi-leaf collimator can move, and therefore at a given dose rate and dose for an arc segment there is a maximum distance they can travel. This is also a constraint in the planning, limiting the quality of the plan.

If the optimisation in the Treatment planning computer was to be allowed to vary the mu per degree, then it would put more dose into gantry angles that have fewer critical organs in the path of the radiation. For example, when treating the prostate, as the gantry rotates the bladder and rectum come in and out of the path of the radiation. It is not possible to avoid irradiating these organs completely, nor is it desirable (otherwise insufficient dose could be deposited into the prostate) but if the optimisation is allowed more flexibility in controlling the dose to these critical organs then it will be able to reduce the unwanted dose.

If the dose rate for the arc can be lowered, this will allow the planning more flexibility but increase the time for delivery, which is undesirable. An aim of this invention is to remove such constraints from the treatment planning process and therefore maximise the quality of the plan, while at the same time retaining a quick delivery time. Quick delivery times are important for departmental efficiency and (in high precision Image Guided Radiation Therapy) to prevent organ motion between imaging and the completion of irradiation.

According to the invention, a desired treatment is therefore described by the Treatment Planning computer in terms of a sequence of "control points". Each "control point" defines a position of the gantry, the dose that is to be delivered between this and the next (or previous) control point, and the shape of the MLC at that control point. Each consecutive pair of control points defines (between them) an arc-segment.

This treatment is put into effect by, between the nth and the $(n+1)^{th}$ control point, moving the gantry from the position of the nth control point to the position of the $(n+1)^{th}$ control point at a rotation speed and a dose rate that combine to deliver the required dose, while moving the MLC leaves so that when the gantry is at the $(n+1)^{th}$ control point, the leaves are in the correct position for that point. Typically, the MLC leaves will be moved at a rate which ensures that at all times their distance moved is linearly related to the dose that has been delivered in the arc-segment. This process is then repeated for the arc-segment between the $(n+1)^{th}$ and the $(n+2)^{th}$ control points, and so on until the treatment is complete.

Thus, we propose a radiotherapeutic apparatus comprising a source able to emit a beam of therapeutic radiation along a beam axis, a multi-leaf collimator arranged to collimate the beam to a desired shape, wherein the source is rotateable about a rotation axis that is substantially orthogonal to and intersects with the beam axis thereby to describe an arc around that axis, further comprising a control means able to control the dose/time rate of the source, the rotation speed of the source, and the multi-leaf collimator position, the control means being arranged to receive a treatment plan in which the arc is divided into a plurality of arc-segments, the treatment plan specifying the total dose for the arc-segment and a start and end MLC position, and to control the source in accordance with that plan over an first arc-segment such that at least one of the rotation speed and dose rate are constant and the multi-leaf collimator changes shape, and a second arc segment such that at least one of the rotation speed and dose rate are constant at a level different to the constant level adopted during the first arc-segment by calculating the total time required for the arc segment for a plurality of factors including an MLC leaf movement from a prescribed position at the start of the arc-segment to a prescribed position at the end of the arc-segment, at a maximum leaf speed, rotation of the source from the start to the end of the arc-segment at a maximum source rotation speed, delivery of the dose at a maximum dose rate per time, selecting the factor dictating the longest time, and controlling the apparatus so that the selected factor operates at its respective maximum and the remaining factors are operated at a reduced rate selected to match that longest time, wherein the total time required for the arc segment for at least one factor relating to a moving geometry item is the greater of (a) a time required to complete the segment if the geometry item travelled at a continuous defined upper speed for the geometry item and (b) a time required to allow for adjustment of the speed of the geometry item until it is travelling at the defined upper speed.

The time required to adjust the speed of the geometry item to the defined upper speed can be determined in a number of possible ways. One option is to perform a calculation via a suitable physics engine or otherwise from first principles, such as from knowledge of the geometry item state and knowledge of its dynamic properties. Another is to determine the time from knowledge of an initial speed and an intended speed of the geometry item by taking a proportion of a time to accelerate the geometry item from rest to the defined upper speed, the proportion being substantially equal to the difference between the initial speed and the intended speed, divided by the defined upper speed. A further option is simply to use a preset amount representing a time to accelerate the geometry item from rest to that speed.

The time required to adjust the speed of the geometry item to the defined upper speed will generally include a time to accelerate the geometry item to that speed, and a further time to accelerate the geometry item beyond that speed and subsequently decelerate it until travelling at that speed. This can be controlled so as to place the geometry item on the same distance/time relationship as if it had changed to that speed instantaneously.

The control means will typically comprise a treatment control computer and an actuator.

The radiotherapeutic apparatus is preferably arranged to monitor the dose actually delivered during a treatment and the actual position of the source and/or MLC, compare this to the treatment plan, and servo the position of the source/MLC and or the dose rate so that the actual relationship between delivered dose and source position corresponds to the treatment plan.

Likewise, the radiotherapeutic apparatus is preferably arranged to monitor the dose actually delivered during a treatment and the actual position of the patient positioning system, compare this to the treatment plan, and servo the position of the patient positioning system and or the dose rate so that the actual relationship between delivered dose and patient positioning system position corresponds to the treatment plan.

The radiation is preferably not interrupted between the first arc-segment and the second arc-segment.

In this way, a system is produced that is sufficiently close to ERDMLC in practice to mean that it can be treated at an ERDMLC system for most purposes. This enables us to further propose a treatment planning apparatus for a radiotherapeutic apparatus of the type comprising (i) a source able to (a) emit a beam of therapeutic radiation along a beam axis and (b) rotate about a rotation axis that is substantially coincident with the beam axis, thereby to describe an arc around that axis, (ii) a multi-leaf collimator arranged to collimate the beam to a desired shape, and (iii) a control means able to control the dose rate of the source, the rotation of the source, and the multi-leaf collimator, the treatment planning apparatus being arranged to divide the arc into a plurality of arc-segments and to prepare a treatment plan which includes a first arc-segment adapted such that through the delivery of a certain number of mu first specified dose during which the source rotates a certain number of degrees first specified angle and the multi-leaf collimator changes shape at a first specified rate per degree, and similarly over a second arc segment adapted to deliver a second specified dose during which the source rotates a second specified angle and the multi-leaf collimator changes shape at a second specified rate per degree, such that at least one of the first and second specified doses, the first and second specified angles, and the first and second specified rates per degree, mu per degree rotation and the mu per mm MLC leaf movement are constant at a level different as between the first and second arc-segments.

It is preferred that the beam axis and the axis of rotation of the source are substantially orthogonal, for reasons of geometric simplicity.

As will be apparent from the above, we prefer that the rotation speed and the dose rate are both constant during an arc-segment, but that at least one thereof is different as between the first arc-segment and the second arc-segment.

Generally, we intend that the first arc-segment and the second arc-segment are consecutive. However, there may be specific instances where individual consecutive arc-segments do in fact have the same rotation speed and dose rate. However, in a treatment plan according to the present invention there will be pairs of arc segments for which at least one is different.

The treatment planning apparatus will of course include an output means of some form, for transmitting the treatment plan to the radiotherapeutic apparatus.

Of course, since much of the calculation effort in this method can be conducted on an assumption of movement at a single steady speed, it is possible to express the various times discussed above in terms of the equivalent distances. Comparisons of the distances are of course directly equivalent to comparison of the associated times.

The treatment planning apparatus can further prescribe a treatment plan that includes motion of a patient positioning system during the treatment, in a manner correlated with motion of the source and/or delivery of the dose. This will (inter alia) allow HIMAT treatments to be provided.

BRIEF DESCRIPTION OF THE DRAWINGS

An embodiment of the present invention will now be described by way of example, with reference to the accompanying figures in which;

FIG. 1 is a graph showing the optimised control points from the Treatment Planning computer as to the leaf position and dose;

FIG. 2 is a graph showing the optimised control points from the Treatment Planning computer as to the gantry position and dose delivered as treatment progresses, and the approximation imposed by a constant mu per degree;

FIG. 3 shows the effect of the control points of FIG. 2, in terms of the dose rate, together with the same approximation;

DETAILED DESCRIPTION OF THE EMBODIMENTS

Figure 4:
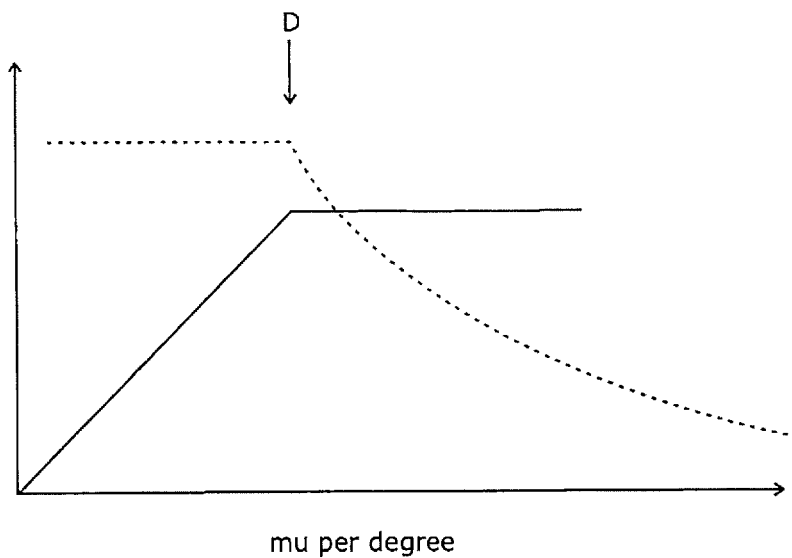
FIG. 4 shows an ideal calculation of the dose rate (solid line) and rotation speed (dashed line)

A desired treatment is described by a Treatment Planning computer in terms of a sequence of "control points". Each "control point" defines a position of the gantry, the dose that is to be delivered between this and the next (or previous) control point, and the shape of the MLC at that control point. Each consecutive pair of control points defines (between them) an arc-segment.

Control points could (in theory) be spaced strategically around the complete arc. However, the availability of relatively cheap processing power means that there is little benefit in going to the effort of doing so, and control points are therefore typically spaced regularly around the arc such as every degree, every few degrees, or every fraction of a degree.

Basic Methodology

This treatment is put into effect by, between the nth and the $(n+1)^{th}$ control point, moving the gantry from the position of the nth control point to the position of the $(n+1)^{th}$ control point at a rotation speed and a dose rate that combine to deliver the required dose, while moving the MLC leaves at a substantially constant rate so that when the gantry is at the $(n+1)^{th}$ control point, the leaves are in the correct position for that point. This process is started at n=1, and then repeated for the arc-segment between the $(n+1)^{th}$ and the $(n+2)^{th}$ control points, and so on until the treatment is complete.

Thus, FIGS. 1 and 2 show a pattern of control points for a treatment. FIG. 1 shows graphically the details of the control points in terms of the position of a specific MLC leaf as the treatment progresses. During the treatment, tracked in terms of the total mu dose delivered so far, the leaf initially extends, retracts, and subsequently extends again. The dotted line shows the instantaneous position of the leaf, given that the control apparatus will move the leaf at a steady rate between control points so that by the time the next point is reached, the leaf is at the desired position. Similar graphs will exist for each of the (typically) 80 leaves; each graph will generally have more than 6 control points, such as 45, 90 or 180 control points.

FIG. 2 shows the details of the control points in terms of total dose delivered as the gantry rotates. Thus, the points are on a monotonically rising scale. However, the amount of the increase between successive control points varies, corresponding to some gantry angles at which more radiation is delivered and some at which less is delivered. The latter will generally correspond to angles at which the target structure is obscured by a critical structure. The variation in dose delivered can be achieved by variation of either the dose rate per time or the gantry rotation speed, or both. Clearly, a reduction in the cumulative dose delivered between a range of positions can be achieved by increasing the rotation speed or by reducing the dose rate. FIG. 2 shows in a dotted line the approximation that is imposed by requiring a constant mu per degree; this reduces the flexibility and either requires a less optimal dose distribution, or requires the variation to be taken up by way of the MLC positions thereby extending the treatment time.

FIG. 3 shows the result of FIG. 2, in terms of the dose rate at each gantry angle. At some gantry angles, the dose rate is high, indicating that a clear view of the target structure is available. At other gantry angles, the dose rate is markedly reduced indicating that the target may be obscured by a critical structure.

Thus, FIGS. 1 to 3 illustrate the treatment plan that is developed by the treatment planning computer, freed of the constraints imposed by previously known apparatus. It now remains for the treatment control computer of the radiotherapy apparatus to translate that treatment plan into a set of gantry moves, dose rates, and MLC moves.

Now, the minimum time in which each arc-segment can be delivered may be defined by the dose or the gantry or any one of the leaves in the MLC. Thus:

Minimum dose time=inter-control point dose/Maximum dose rate,

Minimum gantry time=Distance of gantry move/Maximum gantry speed,

Minimum leaf time=Distance of leaf move/Maximum leaf speed, (considered for each of the moving leaves)

The minimum time for the arc-segment is then the highest of all these minima. This defines the time limiting parameter, which may be the gantry, dose or any of the 80 leaves.

If the dose is not the time limiting parameter, then the desired dose rate can then be selected, being calculated as follows:

Desired dose rate=Control point dose/Minimum time

If the dose is the time limiting parameter, then the selected dose rate is of course the maximum dose rate.

The expected speeds of the Gantry and leaves can then be calculated from the selected dose rate as follows:

Expected arc-segment time=Control point dose/Selected dose rate

Expected gantry speed=Distance of gantry move/Expected arc-segment time and for each of the leaves in the MLC:

Expected leaf speed=Distance of leaf move/Expected arc-segment time

FIG. 4 shows the choice between the dose rate and the gantry speed, ignoring the influence of MLC leaf speed for the purposes of illustration. The x-axis is the dose rate per degree that is achieved, which corresponds to the cumulative dose delivered between two control points. The solid line is the dose rate, while the dotted line is the gantry rotation speed. Both have maximum rates imposed by the limitations of the specific apparatus being used. Thus, there is a specific dose D per unit rotation that is achieved by the apparatus operating at its maximum rotation speed and the maximum dose rate (per unit time).

To achieve a dose per unit rotation that is higher than D, the rotation speed must be decreased in inverse proportion, and the rotation speed (dotted line) in this region therefore shows a 1/x profile while the dose rate (solid line) is steady. To achieve a dose rate per unit rotation lower than D, the dose rate must be reduced proportionately as shown.

FIG. 4 therefore illustrates the above calculations in a graphical form.

It should be noted that some radiotherapeutic apparatus do not actually allow a continuously variable dose rate. Instead, the dose rate is only permitted to adopt one of a number of preset levels. In such a case, the highest available dose rate that is less than the desired dose rate should be selected. The other factors can then be determined as above.

Figure 5:
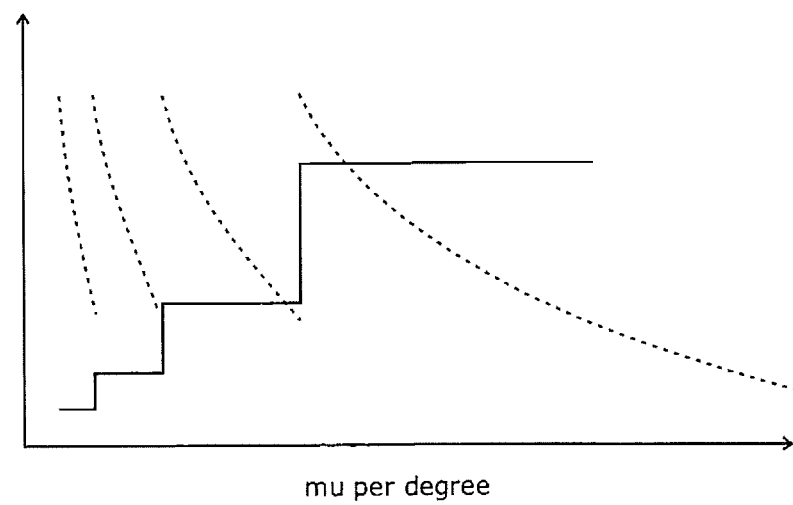
FIG. 5 shows a practical calculation of the dose rate (solid line) and rotation speed (dashed line) in a system without a continuously variable dose rate.

This is illustrated in FIG. 5. This corresponds to FIG. 4 except that in the region of FIG. 4 where the dose rate is linear, the dose rate is forced to increase in steps up to the maximum dose rate. This is compensated for by the rotation speed profile which adopts a series of 1/x curves for each step, instead of simply for the maximum dose rate. Thus, the use of an apparatus without a continuously variable dose rate per unit time incurs a penalty in terms of the treatment time required but not in terms of the dose distribution.

Ideally, the actual positions will be served to the actual delivered dose and therefore the actual speeds will vary slightly from the expected speeds. However, the expected speed is a very useful parameter to ensure that the servos perform optimally.

In this way, a system is produced that is sufficiently close to ERDMLC in practice to mean that it can be treated as an ERDMLC system for most purposes.

Figure 6:
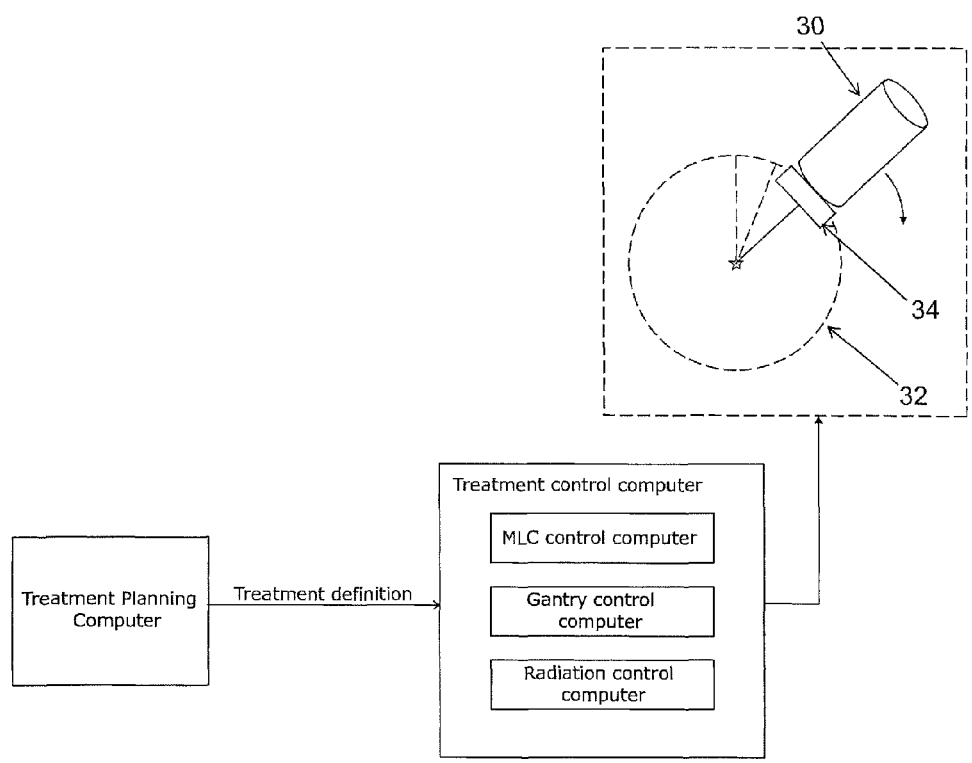
FIG. 6 shows the relationship between the computers.

FIG. 6 shows a radiotherapeutic apparatus demonstrating the relationships between the various computers involved in the system. Shown in the radiotherapeutic apparatus is a radiation source 10 able to emit a beam of therapeutic radiation along a beam axis and a MLC arranged to collimate the beam to a desired shape. Radiation source 10 is able to rotate about a rotation axis to define or describe an arc 12. The beam axis intersects the rotation axis. As shown and described, the arc 12 is divided into a plurality of arc segments (one arc segment is shown). The treatment planning computer develops a treatment plan which defines the treatment and passes this to a treatment control computer. This determines, for each arc-segment, which factor is the time-limiting factor and is thereby able to instruct each of the MLC control computer, gantry control computer, and radiation control computer as to the operation of their specific item during that arc-segment.

In practice, it will be necessary to decide whether each illustrated computer should exist as a separate entity or whether some or all should be combined into a single processor. This decision will depend on the pattern of expected computational load and the processing power available.

Such a treatment plan can be implemented on a radiotherapy machine that is substantially akin to those in current use. The physical differences called for by this invention lie in the control apparatus and the treatment planning apparatus; the actual radiation head and the means for driving it, its MLC and other systems can be as those in current use. However, there are certain changes to the apparatus that could be useful in the context of a machine operating in this manner.

First, the reeling system for the radiation head would benefit from being able to travel more than 360°, such as 2, 3 or more rotations. This would allow an operator to treat 3 or more IMAT arcs without stopping, and also to image and treat the patient in a continuous arc from underneath.

Second, we propose to enclose the whole machine in a set of covers similar in style to a CT or MR machine, with the bore preferably closed off at the inside end. Enclosing the moving parts removes the possibility of a hazardous collision and therefore enables the speed of the gantry to be increased fairly easily from 1 RPM to at least 2 or possibly up to 5 or 6, reducing the treatment times significantly. Increased speed also offers new options for Cone Beam image acquisition for example the images can be acquired during a single breath hold thereby eliminating any artifacts due to breathing motion.

Finally, to further reduce treatment times at high rotational speeds we propose to remove the flattening filters that are normally placed in the path of the beam in order to give a more uniform intensity of radiation across the aperture of the device. These filters do of course act by reducing the intensity of the beam in the central area of the aperture, and therefore the compromise is between uniformity and overall dose. A non-flat or non-uniform beam could instead be characterized and compensated for in treatment planning. This would avoid difficulties relating to the non-uniformity of the beam intensity since adjustments would be made in the other treatment parameters, and would allow a reduction in treatment time commensurate with the "recovery" of radiation that was otherwise removed by the flattening filter.

Inertia Compensation

The above assumes that the elements of the apparatus on which the invention is embodied are idealised geometry items—in other words, that they have no inertia and can therefore be manipulated at will with desired changes to the speed taking effect immediately. In the real world, this is not the case and geometry items have a distinct mass which must be accelerated or decelerated to the desired speed.

If an assumption is made that a geometry item (i.e. a gantry arm, an MLC leaf, or any other part of the apparatus that affects the beam geometry) is inertia-less and that for reasons of efficiency always travels at its maximum design speed, then it follows that its position is predictable via the trivial relationship distance=speed×time, or $s=v_{max} \cdot t$ where $v_{max}$ is the geometry item's maximum design speed.

Given that some time is required to accelerate the geometry item from rest to that speed, there will be an initial period during which the actual speed of the item will be less than the theoretically expected speed. This translates into a lag in the item's position; other factors aside, the actual position at any time would therefore be behind the predicted position by an amount reflecting the item's inertia. That lag can be corrected by continuing to accelerate the item beyond its design speed so that it catches up; whilst this will require the item to exceed its maximum design speed, the excursion will be only brief and is acceptable. The "maximum" design speed is set at a maximum speed at which the item can safely move continuously for an extended period; the maximum safe transient speed will be higher.

Figure 7:
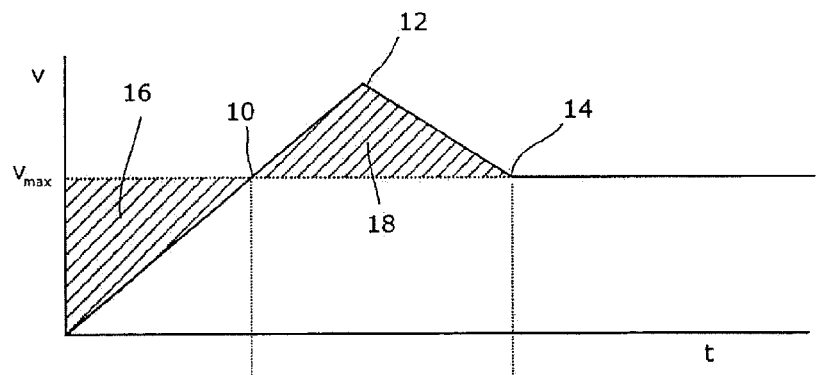
FIGS. 7 and 8 are graphs of (respectively) speed and distance with time, showing the effect of inertia.
Figure 8:
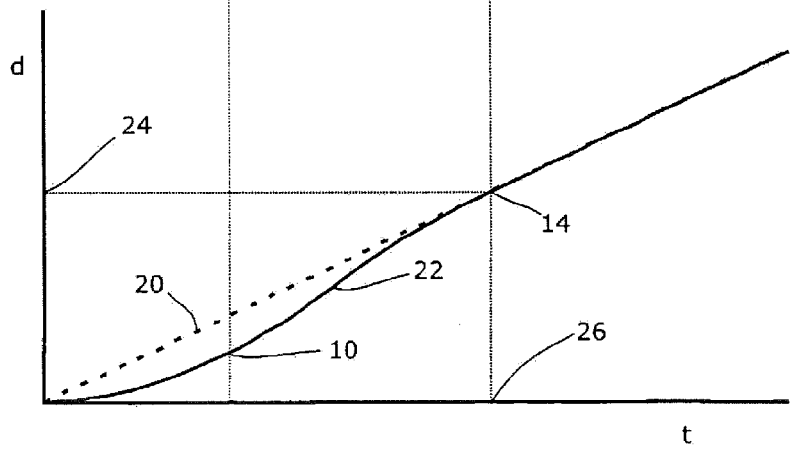

This is shown in FIGS. 7 and 8. FIG. 7 shows the profile of velocity with time. Initially (i.e. t=0), the item is at rest for the purpose of this example and v=0. The item then accelerates at a constant acceleration that is dictated by the power of whatever drives the item and the inertial mass of the item. Thus, the velocity of the item increases smoothly at a constant slope until the point 10 at which it meets the design maximum continuous velocity $v_{max}$. The item is accelerated further up to a peak velocity at 12 representing a maximum transient velocity, after which it is decelerated to $v_{max}$ which it reaches at point 14. Control of the acceleration and deceleration should be by a suitable computation means to ensure that each geometry item is in the correct position with respect to the dose to be delivered. This will mean that the areas 16 and 18 are substantially equal, in which case the lag caused by the acceleration period between t=0 and point 10 will be exactly compensated for by the overspeed between points 10 and 14.

The corresponding plot of distance with time is shown in FIG. 8. As compared to an idealised inertia-free system represented by the dotted line 20, the movement of an actual system (line 22) starts from rest and accelerates, but is constantly behind the ideal line 20. After point 10, the slope of the distance-time curve equals that of the ideal system and thereafter becomes greater, enabling the actual system to catch up. At point 14, the actual system has caught up with the ideal system and can thereafter proceed at the same speed.

This means that there is an initial period in which the position of an actual system is not easily predictable by a straightforward relationship such as $s=v_{max} \cdot t$ but is more complex. Thus, a proper model of the behaviour of the item should take this into account.

An alternative approach takes note of the fact that after the catch-up period between t=0 and 14, the behaviour of the system is predictable. The point 14 at which catch-up is complete and easily predictable behaviors takes over is referred to as the "Inertia Compensation Point" and translates in FIG. 8 to a corresponding "Inertia Compensation Distance" 24 (ICD) and a corresponding "Inertia Compensation Time" 26 (ICT). Provided that the distance or time being modelled is greater than the ICD or ICT respectively, we know that a simple $s=v_{max} \cdot t$ model can be employed.

According to the treatment planning methodology set out above, for each segment a required time is calculated for each factor, i.e. (i) the gantry movement, (ii) the MLC movements, and (iii) the dose delivery, all at the maximum possible rate for each. The longest of these times is then selected; this becomes the time for that segment, and the speeds or rates of the other two are scaled back so that they will take the same overall time for the segment.

To take inertia into account, those factors that have an inertia-related aspect to their modelling can first be modelled using a simple and straightforward linear relationship, and a predicted time for the segment obtained. In addition, for each segment the ICT is determined and compared with this time. The greater of these is then used as the relevant time for that factor over the segment in the above comparison, to determine the rate limiting factor for that segment.

If that time thus chosen for the segment is an ICT, this will mean that all relevant factors will be scaled back accordingly. The non-rate-limiting factors will be scaled back as previously, so that their total time for the segment corresponds to the segment time. The speed of the rate-limiting factor will then also be scaled back so that it completes the segment at less than its maximum speed, at a lower speed that allows time for inertia compensation to take place.

There are a number of different ways in which the ICT can be determined. Ideally, it will be determined for each geometry item in each instance by calculating the ICT for the particular instance concerned based on prior knowledge of the dynamics of the particular system. Other examples, such as a deceleration, acceleration from a non-zero speed to the maximum speed, and acceleration to a speed less than the maximum are also calculable using analogous approaches. Alternatively, it is possible to measure the ICT of the specific example of accelerating a geometry item from rest to its maximum speed in the particular system concerned, and to adopt that as a basic ICT for the acceleration of the item from rest to its maximum speed, i.e. $ICT_{0-max}$. Other ICT values can then be determined by a straightforward scaling process applied to $ICT_{0-max}$. Thus, for a change in speed from Vi to V2, the ICT can then be approximated as:

$$ICT_{v_1 - v_2} = ICT_{0-v_{max}} \left( \frac{|v_1 - v_2|}{v_{max}} \right)$$

As a final alternative, given that all the ICTs are likely to be relatively small, a default ICT can be adopted (such as the $ICT_{0-max}$ above) and used for all geometry items of that type in that system. Provided that a maximal ICT is adopted as the default, this will ensure that a conservative approach is taken in which all geometry items are offered sufficient time to compensate for inertia. It has the difficulty that where the actual ICT is less than the default ICT, the dose rate will be scaled down more than is necessary, thereby lengthening the treatment. In practice, however, the effect of this is likely to be small whereas the use of a default ICT simplifies matters.

Figure 9:
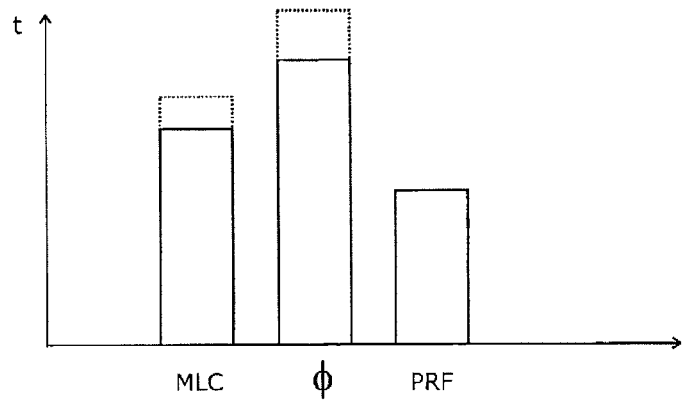
FIGS. 9 to 11 are bar charts showing the comparison process incorporating inertia compensation.
Figure 10:
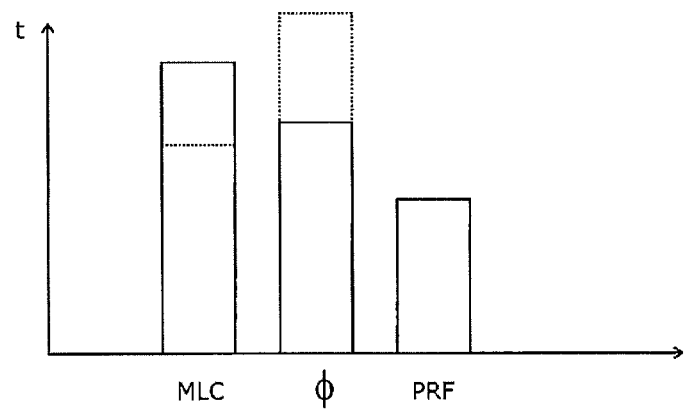
Figure 11:
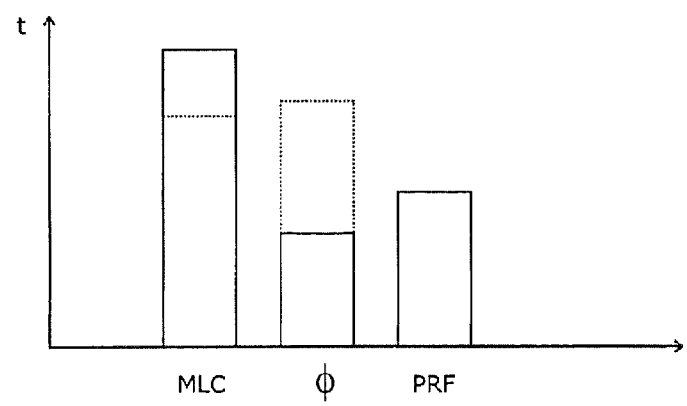

FIGS. 9 to 11 illustrate the inertia-compensated comparison process diagrammatically. Each shows a bar chart representing the time required by each factor for a particular segment. The factors, as discussed above, are the MLC traverse time (labelled "MLC"), the gantry rotation time (labelled "$\Phi$") and the time required to deliver the specified dose at a maximum pulse repetition frequency (labelled "PRF"). On each graph, a dotted bar is also shown for the MLC and gantry rotations representing the Inertia Compensation Time for that segment. This will of course be variable, depending on the speed and position of the respective geometry item at the start of the segment and the required speed (i.e. $v_{max}$) and position at the end of the segment.

Thus, in the example shown in FIG. 9, a simple comparison between the times required by each factor shows the gantry angle $\Phi$ to be the rate-determining step since, of the solid bars, $\Phi$ is the highest. Comparing the dotted bars representing the ICTs, the gantry angle is still the rate determining step, but $ICT_\Phi$ is higher than the predicted time. Thus, the speed of each factor for this segment will need to be scaled down so that the segment time is equal to $ICT_\Phi$. This will ensure that, at the end of the segment, the gantry arm is in the correct position.

FIG. 10 shows an example of a different segment. In this case, a comparison of the solid bars shows that the MLC traverse time is the longest and therefore, using an ideal inertia-less system, this would be the rate-determining factor. However, the Inertia Compensation Time for the gantry angle ($ICT_\Phi$) is greater than the time required for the MLC leaves to traverse, so in the comparison between the times required for different factors, taking into account inertia compensation, it is the gantry angle factor which is the rate-determining step and the segment time is set to be equal to $ICT_\Phi$. Each factor will then be run at a speed or dose rate so that the segment completes in this time.

FIG. 11 shows a comparison in which, without inertia compensation, the MLC traverse time would be the rate determining step. Taking into account the ICTs for the MLC leaves and for the gantry angle, it is apparent that the ICT for the MLC leaves ($ICT_{MLC}$) is less than the predicted time required for the MLC leaves to traverse at their maximum design speed. Therefore, in the comparison between factor times, $ICT_{MLC}$ does not replace the predicted MLC traverse time. In addition, while $ICT_\Phi$ is greater than the predicted time for the gantry to rotate (and is therefore the correct point of comparison in respect of the gantry angle), it is still less than the predicted MLC traverse time. Therefore, the rate-determining factor is the predicted MLC traverse time, and in this segment the MLC leaves will be driven at their maximum design speed and the other factors run at a speed so that they complete the segment in the time dictated by the MLC leaves.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

The invention claimed is:
1. A radiotherapeutic apparatus comprising:
a source able to emit a beam of therapeutic radiation along a beam axis, wherein the source is rotatable about a rotation axis that is substantially orthogonal to and intersects with the beam axis thereby to describe an arc around the rotation axis;
a multi-leaf collimator (MLC) arranged to collimate the beam to a desired shape; and;
a control means able to control a dose/time rate of the source, a rotation speed of the source, and a position of the multi-leaf collimator,
a control means being arranged to receive a treatment plan in which the arc is divided into a plurality of arc-segments, the treatment plan specifying a total dose for an arc-segment and a start and end MLC position, and to control the source in accordance with the treatment plan over an arc-segment by calculating a total time required for the arc segment for a plurality of factors including:
i. an MLC leaf movement from a prescribed position at the start of the arc-segment to a prescribed position at the end of the arc-segment, at a maximum leaf speed;
ii. rotation of the source from the start to the end of the arc-segment at a maximum source rotation speed;
iii. delivery of the dose at a maximum dose rate per time;

the apparatus being arranged to select the factor i, ii, or iii which requires longest time, and to control the apparatus so that the selected factor operates at its respective maximum and the remaining factors are operated at a reduced rate selected to match the longest time wherein the total time required for the arc segment for at least one factor relating to a moving geometry item is the greater of (a) a time required to complete the arc segment if the geometry item travelled at a continuous defined upper speed for the geometry item and (b) a time required to allow for adjustment of the speed of the geometry item until it is travelling at the defined upper speed.

2. The radiotherapeutic apparatus according to claim 1 in which the time required to adjust the speed of the geometry item to the defined upper speed is calculated from knowledge of the geometry item state and knowledge of its dynamic properties.

3. The radiotherapeutic apparatus according to claim 1 in which the time required to adjust the speed of the geometry item to the defined upper speed is calculated from knowledge of an initial speed and an intended speed of the geometry item by taking a proportion of a time to accelerate the geometry item from rest to the defined upper speed, the proportion being substantially equal to the difference between the initial speed and the intended speed, divided by the defined upper speed.

4. The radiotherapeutic apparatus according to claim 1 in which the time required to adjust the speed of the geometry item to the defined upper speed is a preset amount representing a time to accelerate the geometry item from rest to that speed.

5. The radiotherapeutic apparatus according to claim 1 in which the time required to adjust the speed of the geometry item to the defined upper speed includes a time to accelerate the geometry item to that speed, and a further time to accelerate the geometry item beyond that speed and subsequently decelerate it until travelling at that speed.

6. The radiotherapeutic apparatus according to claim 1 wherein the control means comprises a treatment control computer and an actuator.

7. The radiotherapeutic apparatus according to claim 1 in which the radiation is not interrupted between the first arc-segment and the second arc-segment.

8. The radiotherapeutic apparatus according to claim 1 arranged to monitor the dose actually delivered during a treatment and the actual position of the source, compare this to the treatment plan, and servo the position of the source and or the dose rate so that the actual relationship between delivered dose and source position corresponds substantially to the treatment plan.

9. The radiotherapeutic apparatus according to claim 1 arranged to monitor the dose actually delivered during a treatment and the actual position of the MLC, compare this to the treatment plan, and servo the position of the MLC and or the dose rate so that the actual relationship between delivered dose and MLC position corresponds substantially to the treatment plan.

10. The radiotherapeutic apparatus according to claim 1 arranged to monitor the dose actually delivered during a treatment and the actual position of the patient positioning system, compare this to the treatment plan, and servo the position of the patient positioning system and or the dose rate so that the actual relationship between delivered dose and patient positioning system position corresponds substantially to the treatment plan.

11. A treatment planning apparatus, for a radiotherapeutic apparatus of the type comprising (i) a source able to (a) emit a beam of therapeutic radiation along a beam axis and (b) rotate about a rotation axis that intersects the beam axis thereby to describe an arc around the rotation axis, (ii) a multi-leaf collimator arranged to collimate the beam to a desired shape, and (iii) a control means able to control a dose rate of the source, a rotation of the source, and the multi-leaf collimator;

the treatment planning apparatus being arranged to divide the arc into a plurality of arc-segments and to prepare a treatment plan which includes a first arc-segment, adapted to deliver a first specified dose during which the source rotates a first specified angle and the multi-leaf collimator changes shape at a first specified rate per degree, and a second arc segment adapted to deliver a second specified dose during which the source rotates a second specified angle and the multi-leaf collimator changes shape at a second specified rate per degree, such that at least one of the first and second specified doses, the first and second specified angles, and the first and second specified rates per degree differ as between the first and second arc-segments wherein the total time required for the arc segment for at least one factor relating to a moving geometry item is the greater of (a) a time required to complete the segment at a continuous defined upper speed for the geometry item and (b) a time required to accelerate the geometry item until it is travelling at the defined upper speed.

12. The treatment planning apparatus according to claim 11 in which the time required to adjust the speed of the geometry item to the defined upper speed is calculated from knowledge of the geometry item state and knowledge of its dynamic properties.

13. The treatment planning apparatus according to claim 11 in which the time required to adjust the speed of the geometry item to the defined upper speed is calculated from knowledge of an initial speed and an intended speed of the geometry item by taking a proportion of a time to accelerate the geometry item from rest to the defined upper speed, the proportion being substantially equal to the difference between the initial speed and the intended speed, divided by the defined upper speed.

14. The treatment planning apparatus according to claim 11 in which the time required to adjust the speed of the geometry item to the defined upper speed is a preset amount representing a time to accelerate the geometry item from rest to that speed.

15. The treatment planning apparatus according to claim 11 in which the time required to accelerate the geometry item to the defined upper speed includes a time to accelerate the geometry item to that speed, and a further time to accelerate the geometry item beyond that speed and subsequently decelerate it until travelling at that speed.

16. The treatment planning apparatus according to claim 11 in which the rotation speed and the dose rate both constant during an arc-segment, and at least one thereof is different as between the first arc-segment and the second arc-segment.

17. The treatment planning apparatus according to claim 11 in which the first arc-segment and the second arc-segment are consecutive.

18. The treatment planning apparatus according to claim 11, further comprising an output means for transmitting the treatment plan to the radiotherapeutic apparatus.

19. The treatment planning apparatus according to claim 11 arranged to calculate an irradiation time for each arc-segment apt to deliver a required dose and to infer a rotation speed from the irradiation time.

20. The treatment planning apparatus according to claim 11 arranged to prescribe a treatment plan that includes motion of a patient positioning system during the treatment in a manner correlated with motion of the source.

21. The treatment planning apparatus according to claim 11 arranged to prescribe a treatment plan that includes motion of a patient positioning system during the treatment in a manner correlated with delivery of the dose.

22. The treatment planning apparatus according to claim 11 in which the beam axis and the axis of rotation of the source are substantially orthogonal.

* * * * *

UNITED STATES PATENT AND TRADEMARK OFFICE
CERTIFICATE OF CORRECTION

PATENT NO. : 8,503,608 B2  Page 1 of 1
APPLICATION NO. : 12/739206
DATED : August 6, 2013
INVENTOR(S) : Brown et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 319 days.

Signed and Sealed this
Fifteenth Day of September, 2015

Michelle K. Lee
*Director of the United States Patent and Trademark Office*